United States Patent [19]

Takenaka et al.

[11] 4,214,356
[45] Jul. 29, 1980

[54] ARTIFICIAL PORCELAIN TOOTH MANUFACTURING

[75] Inventors: Susumu Takenaka, Osaka; Hideo Ishii, Toyonaka; Masao Katooka, Ikeda, all of Japan

[73] Assignee: Sansha Electric Manufacturing Co., Ltd., Osaka, Japan

[21] Appl. No.: 874,498

[22] Filed: Feb. 2, 1978

[30] Foreign Application Priority Data

Feb. 7, 1977 [JP] Japan .................. 52-12769

[51] Int. Cl.² .................................................. B21F 43/00
[52] U.S. Cl. .................................. 29/160.6; 433/218; 29/527.2; 29/527.4; 29/527.5
[58] Field of Search ............ 425/174.2, 174.8 R, 425/180, 432, 421, 424, 456; 32/12, 13; 29/527.4, 527.2, 527.5, 160.6

[56] References Cited

U.S. PATENT DOCUMENTS

| 2,700,810 | 1/1955 | Garni | 425/432 |
| 3,456,295 | 7/1969 | Torigai et al. | 425/174.2 |
| 3,506,062 | 4/1970 | Hoffman | 425/174.2 |
| 3,520,961 | 7/1970 | Suda et al. | 425/174.8 |
| 4,104,798 | 8/1978 | Takahashi et al. | 32/12 |

Primary Examiner—Robert Peshock
Attorney, Agent, or Firm—Eugene E. Geoffrey, Jr.

[57] ABSTRACT

The method and apparatus for manufacturing an artificial tooth crown which involves the formation of a metal crown, coating the crown with porcelain materials and subjecting the coated crown to high frequency vibrations of the order of 15 to 50 Hz to condense the porcelain materials and remove air and liquid therefrom prior to firing.

2 Claims, 7 Drawing Figures

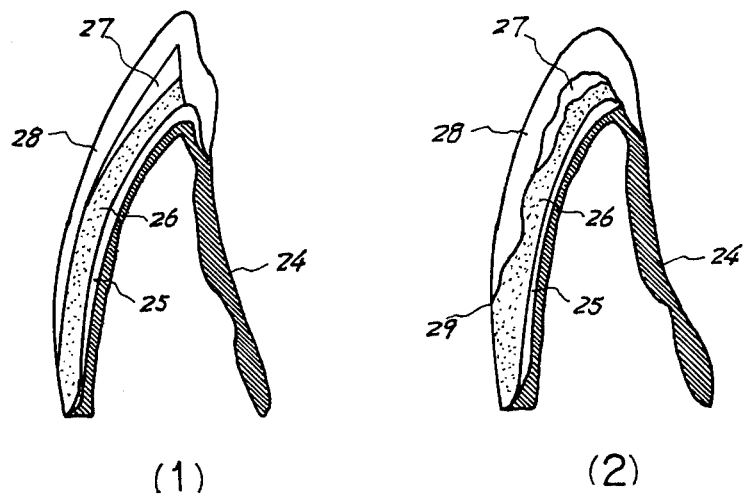
FIG. 6
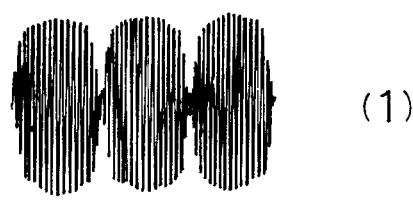
(1)
FIG. 7
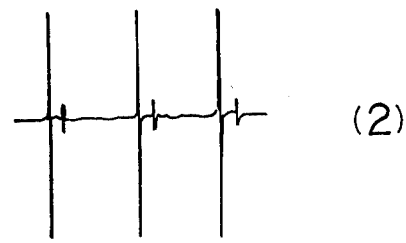
(2)
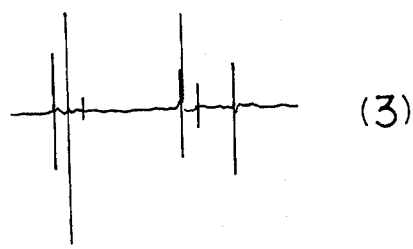
(3)

ARTIFICIAL PORCELAIN TOOTH MANUFACTURING

This invention relates generally to an artificial tooth manufacturing device and more particularly, to a device for applying vibration to a tooth crown having porcelain materials built up thereon to facilitate condensation of the porcelain materials.

In manufacture of an artificial tooth, dental porcelain materials are built up on a metal crown prepared by molding or forming from a metal sheet, successively in several layers. After building up and correcting the shape, the built-up body is fired at a predetermined temperature. While the porcelain materials are used as mixture with water or other solutions, it is essential to remove sufficiently air contained in the porcelain materials built up on the crown, during the building-up process, because the air left in the materials may result in a lot of pores produced during the firing process, which, in turn, may result in reduced transparency affecting natural feeling and reduced mechanical strength. It is also necessary, before firing, to remove excessive liquid from the built-up porcelain materials by expelling it to the surface so that it can be absorbed with gauze or the like, because it may interfere with condensation of the porcelain materials and result in deformation during working and in contraction and deformation upon firing.

According to the prior art technique, in order to expel the interior air and liquid, it has been a general practice to apply shock or vibration to the built-up porcelain materials by pinching the tooth crown with a forceps or the like and then tapping the forceps with a spatula or the like. However, this kind of work has required great skill and, consequently, resulted in an excessive time for working and increased failure.

Japanese Utility Model Publication No. 50-8479 disclosed a novel vibration device to be used for this application. This device comprises a handy cylindrical pencil-type casing including an electromagnet and a working tool coupled to the electromagnet. With application of commercial frequency current to the electromagnet, the working tool is put in contact with a metal crown having porcelain materials built up and being held with an appropriate tool such as forceps in the other hand. Although some advantages have been gained by this device, as compared with the aforementioned classic tapping method, it has still been disadvantageous since it is considerably heavier than the normal tools and has a burdensome electric cord extending therefrom. Moreover, it has been unsuitable for vibrating the whole built-up body or plaster model on which such bodies are mounted, since it used to apply vibration only to a portion being in contact with the vibrating tool. Furthermore, the such commercial frequency device has not only caused deformation of the built-up body, but it has also been disagreeably noisy.

Accordingly, an object of this invention is to provide a vibrating device which is free from the above-mentioned disadvantages of the prior art techniques.

This object is attained by the device according to this invention. One feature of this invention is the use of ultrasonic driving of a supporting member or an object to be worked, and another feature is a table-type structure of the device.

These and other features and advantages of this invention will be described in detail hereinunder with reference to the accompanying drawings.

IN THE DRAWINGS

Figure 1:
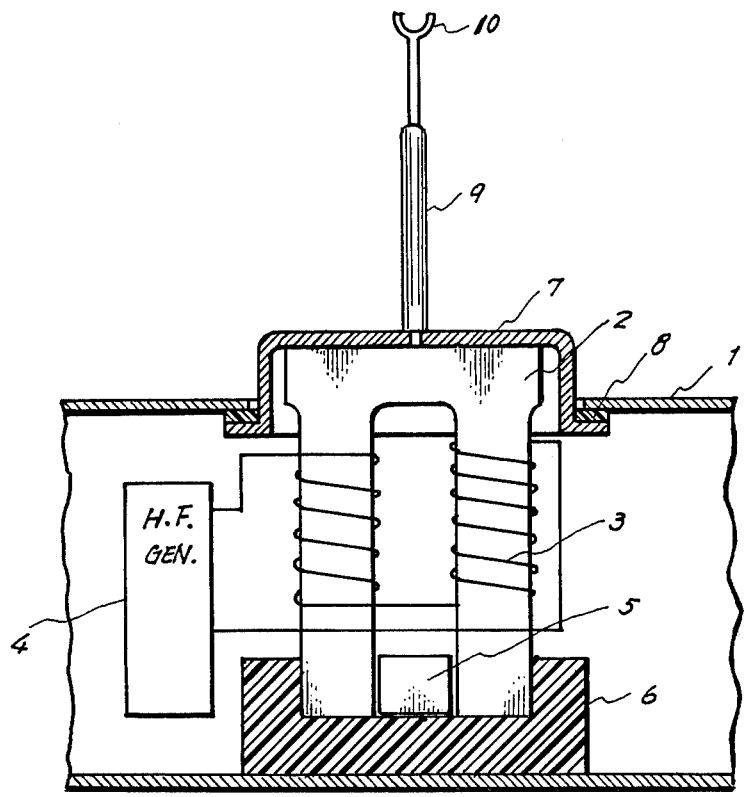
FIG. 1 is a schematic cross sectional view representing an essential part of an embodiment of the device according to this invention.
Figure 2:
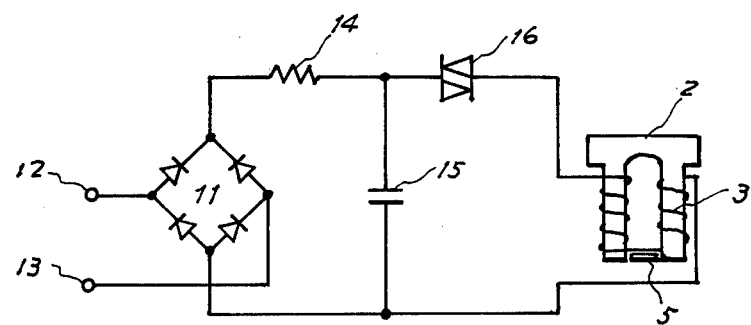
FIG. 2 is a schematic circuit diagram representing a high frequency generator circuit used in the device of FIG. 1.
Figure 3:
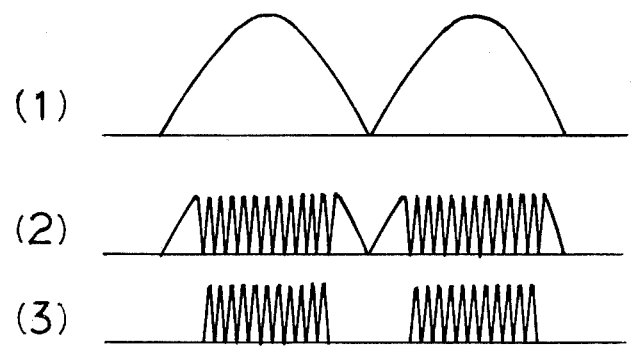
Figure 4:
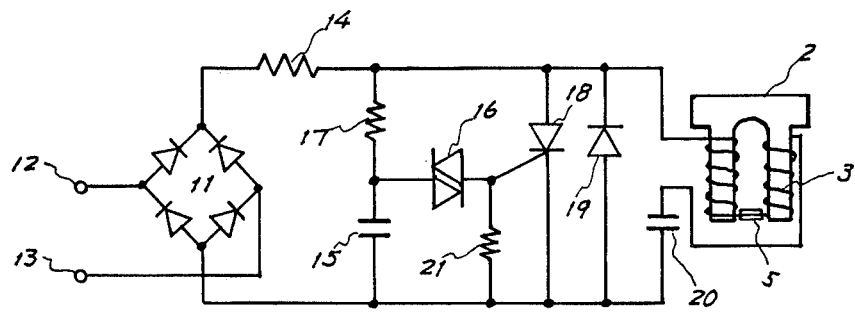
Figure 5:
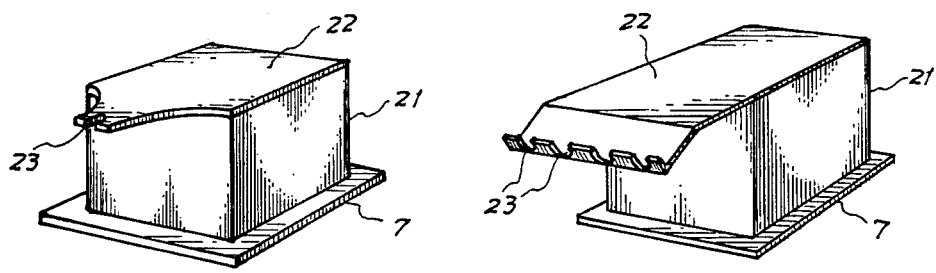

FIG. 3 (1), (2) and (3) are waveform diagrams presented as an aid to explain the operation of the circuit of FIG. 2;

FIG. 4 is a circuit diagram representing another embodiment of the high frequency generator circuit usable in the device of FIG. 1;

FIG. 5 (1) and (2) are perspective views representing two embodiments of a vibrating member in accordance with the invention alternatively usable with the device of FIG. 1;

FIG. 6 (1) and (2) are sectional side views of two examples of a built-up body of artificial tooth; and FIG. 7 (1), (2) and (3) are waveform diagrams presented as an aid to explain the improved function of the device of this invention.

Throughout the drawings, like reference numerals are used to denote like structural components.

Referring to FIG. 1, the device of this invention comprises a housing 1 containing a U-shaped magnetostrictive vibrator 2 having a driving winding 3 connected to a high frequency generator 4. A d.c. biasing permanent magnet 5 is disposed between the both legs of the vibrator 2. The vibrating base member 7 is fixed to the top face of the vibrator 2 and also to the housing 1 through a resilient spacer 8. A support rod 9 having a forked member 10 at the top is fixed to the vibrating member 7. The forked member 10 is so shaped that working tools as described later can engage therewith.

Referring next to FIG. 2, the high frequency generator 4 of FIG. 1 includes a conventional full-wave rectifier circuit 11 having input terminals 12 and 13 connected to a commerical power supply (not shown). A series connection of a current limiting resistor 14 and an oscillation capacitor 15 is connected between the output terminals of the rectifier circuit 11, and a series connection of a switching element 16 and the driving winding 3 of the electromagnet 2 is connected across the capacitor 15.

In operation, a commercial frequency voltage, for example, of 50 or 60 Hz, is applied to the input terminals 12 and 13 and a rectified voltage, as shown in FIG. 3 (1), is obtained from the rectifier circuit 11. This voltage is limited by the limiting resistor 14 and applied to the capacitor 15, thereby producing an oscillation voltage, as shown in FIG. 3 (2), across the capacitor 15, which is, in turn, shaped by the switching element 16 into a waveform as shown in FIG. 3 (3) and applied to the driving winding 3. The frequency of the driving voltage FIG. 3 (3) is, for example, about 15 to 50 KHz, which is selected to be comparable with the resonance frequency of the vibrator 2.

A more practical circuit for the high frequency generator 4 (FIG. 1) is shown in FIG. 4. This circuit is different from that of FIG. 2 in that a resistor 17 is inserted in series with the series connected of the current limiting resistor 14 and oscillation capacitor 15 and a parallel connection of the conduction path of a thyrister 18, a diode 19 and a series connection of the driving winding 3 and a capacitor 20 is connected across the series connection of the resistor 17 and the capacitor 15. The capacitor 15, is shunted by a series connection of a switching element 16 and a resistor 21, with the junction therebetween being connected to the control terminal of the thyrister 18. This circuit can produce a high frequency voltage as shown in FIG. 3 (3) in the case of the circuit of FIG. 2. As the operation of the circuit is self-explanatory to those skilled in the art, further description is not deemed necessary.

When the high frequency generator 4 is actuated, the magnetostrictive vibrator 2 vibrates at its resonance frequency comparable with the high frequency output of the generator 4, which can be referred to as the "ultrasonic frequency". This vibration is transferred through the basic vibrating member 7 to the support rod 9 and forked member 10. If the metal crown having porcelain materials built up thereon is held with an appropriate holding tool, such as forceps or pincette, and the tool is fitted into the depression of the forked member 10, the vibration is transferred in turn through the holding tool and metal crown to the porcelain materials on the crown. Accordingly, in this case, all of the porcelain materials built up on the crown are subjected concurrently to the ultrasonic vibration.

As occasion demands, the support rod 9 may be substituted with any member suitable for working. FIG. 5 (1) and (2) show two alternates, including a block 21 fixed on the base member 7 and a plate 22 fixed to the block 21 and provided with a single or plurality of depressions 23 at an end thereof.

FIG. 6 (1) shows the ideal contour of four porcelain layers 25, 26, 27 and 28 built up on a metal crown 24. The crown 24 is cast in a mold or formed from a metal sheet. The first layer 25 is an opaque one for shielding the metallic color of the crown 24 and is fired prior to application of the other layers. The second, third and fourth layers 26, 27 and 28 are body-colored, incisal-colored and translucent layers, respectively, and are successively built up on the first layer 25 without any intervening firing step. After these layers are completely built up, the whole body is fired in a predetermined condition.

As the porcelain materials are in slurry state, they tend to flow down during being built up. In order to suppress this undesirable tendency, vibration is applied thereto for expelling air and liquid out of the layers so as to facilitate or accelaerate condensation or settlement of the porcelain materials. If the condensation is made roughly, the built-up layers are easy to deform in both surface and interface and the interface edge 29 between the layers 26 and 28 tends to undesirably rise, as shown in FIG. 6 (2).

As stated in the preface, according to the prior art technique, even in the case of using a commercial frequency source, condensation was done roughly and rendered the built-up layers deformed. Although attempts have been made to decrease the amplitude of vibration to reduce this tendency of deformation, the condensation efficiency was almost lost. Accordingly, it has been difficult to obtain an ideal contour as shown in FIG. 6 (1), and the finished product has often been not only degraded in shape but also unsatisfactory in color and mechanical strength.

The inventors have found that the condensation effect is significantly improved by using ultrasonic frequency for the vibration. More particularly, when ultrasonic frequency is used, fine and uniform condensation is obtained. Therefore, it is much easier to obtain the ideal contour of FIG. 6 (1) than with prior art techniques, and the finished product exhibits superior color, clearness and mechanical strength.

FIG. 7 (1), (2) and (3) show waveforms displayed on a cathode ray tube, which were picked up from a metal crown subjected to various vibrations. Ultrasonic vibration was applied by the device of this invention in FIG. 7 (1), while commercial frequency vibration was applied by an electromagnet device of the prior art in FIG. 7 (2). In FIG. 7 (3), the classic tapping method was used. These waveforms teach that there is not essencial difference between the cases of FIG. 7 (2) and (3), except the uniformity of shocks, but a great difference exists between the case of FIG. 7 (1) and the other cases. As shown, although the envelope frequency of the waveform of FIG. 7 (1) is same as the commercial frequency, such as 60 Hz, of FIG. 7 (2), it includes an ultrasonic carrier frequency which is comparable with the driving high frequency, such as 28 KHz. This means that the worked object is subjected to substantial vibration in the device of this invention but only to repeated shocks with the prior art techniques, and is indicative of the reason for the improvement according to this invention.

The improved condensation according to this invention is considered to be owing to coagulation effect of ultrasonic vibration, which suppresses classification of particles to conserve uniformity of the particle size distribution, and the efficient air expelling or deaerating effect is considered to be owing to the ultrasonic vibration, which catches air dissolved in the porcelain materials as fine bubbles and expels them immediately to the surface. These functions can be proved by the extremely fine texture, uniform color and high clearness or transparency of the fired product of this invention. On the contrary, according to the prior art technique, due to classification of particles taking place, the fired product exhibits less uniform texture, degraded color and lower mechanical strength.

Although the above description has been made in conjunction with the embodiment utilizing a magnetostrictive vibrator or transducer, it should be noted that this invention may be embodied by utilizing an electrostrictive or other ultrasonic vibrators or transducers. Furthermore, other modifications and changes can be made by those skilled in the art without departing from the spirit and scope of this invention.

What is claimed is:

1. The method of manufacturing an artificial porcelain coated metal dental crown comprising the steps of forming a metal crown by casting, drawing and the like, applying an opaque layer to at least a portion of the metal crown to shield the color of the metal, applying at least one layer of a slurry containing porcelain materials in overlying relationship to coat said opaque layer, vibrating said metal crown with said layers thereon at an ultrasonic frequency to condense said porcelain materials and expel air and liquid therefrom and then firing the coated metal crown to form the completed dental crown.

2. The method of manufacturing an artificial porcelain coated metal dental crown according to claim 1 wherein the frequency of said ultra-sonic vibration is in the range of 15 to 50 KHz.

* * * * *